(12) United States Patent
Jancik, Jr.

(10) Patent No.: US 6,347,634 B1
(45) Date of Patent: Feb. 19, 2002

(54) METHOD FOR INCREASING PROBABILITY OF CONCEPTION OF CHILD OF DESIRED SEX

(75) Inventor: Francis J. Jancik, Jr., Vale, NC (US)

(73) Assignee: Hand-up Co., Inc., Vale, NC (US)

( * ) Notice: Subject to any disclaimer, the term of this patent is extended or adjusted under 35 U.S.C. 154(b) by 0 days.

(21) Appl. No.: 09/374,768

(22) Filed: Aug. 16, 1999

Related U.S. Application Data

(63) Continuation of application No. 08/499,813, filed on Jul. 10, 1995, now abandoned.

(51) Int. Cl.$^7$ .............................................. A61B 19/00
(52) U.S. Cl. ...................................... 128/899; 600/549
(58) Field of Search ......................... 128/899; 600/549, 600/555, 33, 35

(56) References Cited

U.S. PATENT DOCUMENTS 4,849,885 A     7/1989   Stillwagon et al.

OTHER PUBLICATIONS

Wittles et al.; "A Note on Stress and Sex Determination", 1974, vol. 124(2), pp. 333–334; Journal of Genetic Psychology.

*Primary Examiner*—Cary O'Connor
*Assistant Examiner*—Ryan Carter

(74) *Attorney, Agent, or Firm*—Adams, Schwartz & Evans, P.A.

(57) ABSTRACT

A method of increasing the probability that a woman will conceive either a male child or a female child, comprising the steps of determining an infrared body temperature of the father, determining an infrared body temperature of the mother, categorizing the determined infrared body temperatures of the mother and the father as either "high" or "low" according to a predetermined categorization criteria, and correlating the stress level of the mother and the father according to a correlation where in the case of high temperature for both the mother and the father, the probability of a male child is greater than the probability of a female child; in the case of high temperature for one of the mother or the father and low temperature for the other of the mother or the father, the probability of a male child is greater than the probability of a female child; and in the case of low temperature for both the mother and the father, the probability of a male child is less than the probability of a female child. The information derived is applied by using the sex probabilities according to the criteria where procuring conception of the child without alteration of the infrared body temperature of the mother and father if the indicated probability of conceiving a male or female child favors the mother and father's preference, or procuring conception of the child after altering the infrared body temperature of the mother and/or father to increase the indicated probability of conceiving a child of the sex preferred by the mother and father.

1 Claim, 2 Drawing Sheets

(2 of 2 Drawing Sheet(s) Filed in Color)

METHOD FOR INCREASING PROBABILITY OF CONCEPTION OF CHILD OF DESIRED SEX

This application is a continuation of Ser. No. 08/499,813, filed Jul. 10, 1995, now abandoned.

TECHNICAL FIELD AND BACKGROUND OF THE INVENTION

This invention relates to a method of increasing the probability of a female parent conceiving a child of the desired sex, by use of infrared radiation analysis. This method has application by medical personnel during individual counseling of couples wishing to increase the probability of having either a boy or a girl, as well as by government officials as a part of population control practices. Use of the technique described in this application will substantially reduce both abortion and the birth of additional children of one sex while the parents are trying to conceive a child of the opposite sex.

Techniques for enhancing the probability of conceiving a child of a predetermined sex are known. In general, these techniques involve manipulating the father's sperm to either increase the percentage of sperm carrying the genetic material for either a male or female offspring exposed to the mother's egg for fertilization, or altering the motility of the sperm so that sperm carrying the desired genetic material have an increased probability of fertilizing the egg.

In one technique, the father's semen is extracted and the sperm are caused to swim through a viscous substance in a laboratory test tube. Sperm having an X-chromosome, which produce females, are larger than the Y-chromosome bearing sperm which produce males. The Y-chromosome sperm swim faster, and so can be separated from the X-chromosome sperm. The result is two semen samples—one rich in X-chromosome sperm and one rich in Y-chromosome sperm. One or the other sample is then inseminated artificially into the mother.

The other technique is extract semen from the father and eggs from the mother, fertilize the eggs in vitro, and then analyze the DNA of the fertilized eggs to determine which of the embryos are male and which are female. Then, a embryo having the desired sex is implanted into the mother's uterus. This procedure is very expensive, and is ordinarily used in instances where parents want to avoid passing along to their children sex-linked diseases or defects, such as muscular dystrophy or hemophilia. Because of ethical and technological concerns, it is normally not used when parents merely prefer one sex to the other.

These techniques require artificial insemination. In other words, the semen is obtained from the father, manipulated according to one of several techniques, and then introduced into the mother's womb in precise timing with ovulation. These medical techniques are quite expensive and time-consuming and convert normal and natural mating into a medical procedure devoid of normal human reproductive interaction.

Other techniques, such as douching with acidic or basic liquids before intercourse, have not been proven to improve the probabilities of a child of one or the other sex being conceived.

Infrared analysis of human beings has be common for many years. Many medical procedures, such as determining blood circulation efficiency and the location of tumors, rely on thermographs taken of parts of the human body. Human skin is an almost perfect absorber, and hence, emitter of infrared radiation. With a perfect emitter of infrared radiation defined as having an emissivity index of 1.00, human skin has an emissivity index of 0.98. This means infrared radiometric techniques are relatively simple and accurate when used in measuring the temperature of human skin.

Infrared temperature measurement is carried out with an infrared scanning device. The scanning field is optically scanned point by point to create a mosaic picture. This happens at a scan rate sufficiently rapid that the image generated appears instantaneous and continuous, as in a television picture. A typical infrared scanner acquires infrared radiation from the target and reflects the radiation onto a vertical oscillating mirror which reflects it upwardly to a horizontally oscillating mirror. From the horizontal mirror the radiation is reflected downwardly to a 450 degree angled mirror which sends the beam of radiation to lens which focusses it onto the detector. The infared beam is converted to an electrical signal which is amplified and processed electronically into a television-type picture. Infrared detectors use either Indium Antimonide or Mercury Cadmium Telluride as the detecting crystal. The invention of this application works with either type.

In general, the method according to the invention operates on the principle that there is a relatively high correlation between the infrared body temperature of human beings and the effect of that temperature on the probability of either a X-chromosome (female gender determining) or Y-chromosome (male gender determining) sperm achieving union with the female's egg. While there is much that is not known about the effects of temperature, stress and similar human characteristics on sperm behavior, it is known that human stress levels are reflected in varying infrared body temperatures, and that body temperature has an effect on sperm motility and survival.

The inventive method according to this application permits a couple desiring to have either a male or female child to increase the probability of doing so without expensive and complicated medical procedures, and in a manner more in keeping with normal human reproductive activities.

SUMMARY OF THE INVENTION

Therefore, it is an object of the invention to provide a method of increasing the probability of a female parent conceiving a child of the desired sex by use of infrared radiation analysis.

It is another object of the invention to provide a method of increasing the probability of a female parent conceiving a child of the desired sex which avoids costly medical treatments and techniques.

It is another object of the invention to provide a method of increasing the probability of a female parent conceiving a child of the desired sex which permits the parents to reproduce in a normal human manner, and particularly without any form of artificial insemination.

It is another object of the invention to provide a method of increasing the probability of a female parent conceiving a child of the desired sex which utilizes information regarding the infrared temperature of the parents.

These and other objects of the present invention are achieved in the preferred embodiments disclosed below by providing a method of increasing the probability that a woman will conceive either a male child or female child, comprising the steps of determining a baseline stress level of the father, determining a baseline stress level of the mother, categorizing the determined stress levels of the mother and the father as either "high" or "low" according to a predetermined categorization criteria, and correlating the stress level of the mother and the father according to a correlation where in the case of high stress for both the mother and the father, the probability of a male child is greater than the probability of a female child is, with increased possibilities of infertility or miscarriage; in the case of high stress for one of the mother or the father and low stress for the other of the mother or the father, the probability of a male child is greater than the probability of a female child in the case of low stress for both the mother and the father, the probability of a male child is less than the probability of a female child. The information derived is applied by utilizing the sex probabilities according to the criteria where procuring conception of the child without alteration of the stress level of the mother and father if the indicated probability of conceiving a male or female child favors the mother and father's preference, or procuring conception of the child after altering the normal stress level of the mother and/or father to increase the indicated probability of conceiving a child of the sex preferred by the mother and father.

According to one preferred embodiment of the invention, the step of determining the stress level of the mother and the father comprises determining the infrared temperature of a body appendage of each.

According to another preferred embodiment of the invention, the body appendages are a mother's hand and a father's hand.

According to yet another preferred embodiment of the invention, the step of procuring conception of the child after altering the normal stress level of the mother and/or father includes the step of prescribing medication to reduce the indicated stress level.

According to yet another preferred embodiment of the invention, the step of procuring conception of the child after altering the normal stress level of the mother and/or father includes the step of prescribing medication to increase the indicated stress level.

According to yet another preferred embodiment of the invention, wherein the steps of determining the stress level of the mother and the father comprise scanning a hand of the mother and a hand of the father with an infrared scanner.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

The method according to the preferred embodiment of this invention is carried out using an infrared thermograph, preferably a Model 535 computerized medical thermograph manufactured by Inframetrics, Billerica, Mass. Other thermographs may also be used. The Model 535 is particularly suitable because it provides 4x zoom, computerized temperature measurement and calculation, long wavelength infrared detection using a Mercury-Cadmium-Telluride detector. The thermograph is operated in accordance with standard procedures as set out in the Model 535 "Medical Thermograph Operator's Manual, available through Adler & Hruska of Sherman Oaks Calif.

The method operates on the principle that the human hand can be scanned directly to obtain an indication of stress levels being experienced by the patient. The hand is very rich in blood vessels close to the surface, and thus provides a convenient body appendage from which to obtain a very accurate thermographic picture. The use of the "stress" terminology is only for convenience, and the categorization of a person as having a high or low "stress" level as measured by the thermograph does not mean that the person exhibits traits necessarily associated with stress pathology. The important determinant is the infrared temperature detected by the thermograph.

After proper adjustment of the thermograph according to instructions, the hand of the mother and the father is scanned to determine an isotherm temperature. An isotherm ("ISO") is a thermal contour line, all points of which are the same temperature. The ISO measurement provides an indication of relative stress level of the subject, according to the following values:

High Stress—33.7° C. to 36° C.

Low Stress—29° C. to 33.6° C.

The average High Stress temperature is 34° C., and the average Low Stress temperature is 32° C. This compares with normal human body core temperature of 37° C., or 98.6° F.

Figure 1:
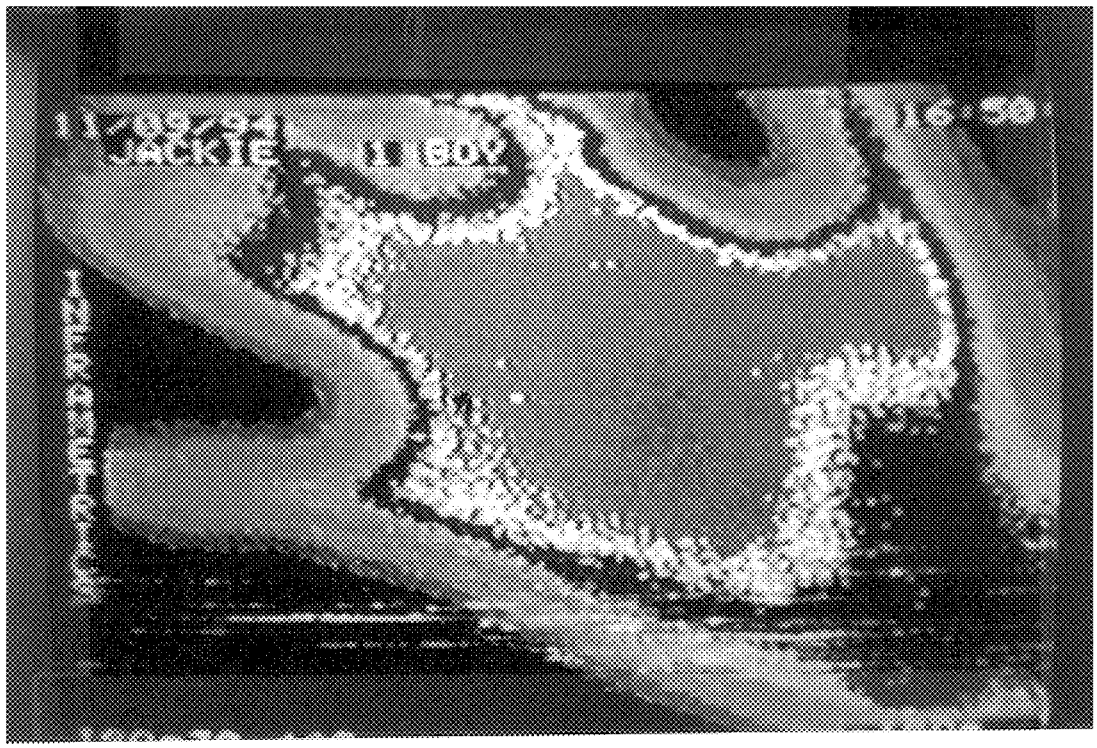
FIG. 1 is a color photograph of a thermogram of a human hand with an isotherm in the "high stress" zone indicative of a "high stess" individual.
Figure 2:
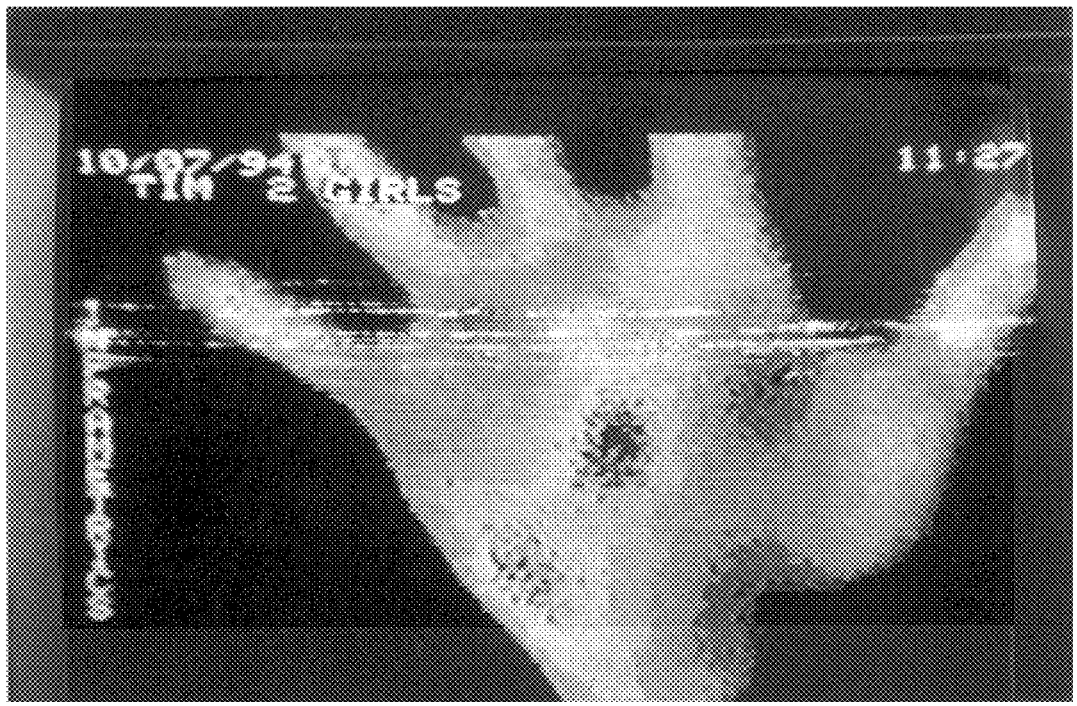
FIG. 2 is a color photograph of a thermogram of a human hand with an isotherm in the "low stress" zone indicative of a "low stess" individual.

As shown in FIGS. 1 and 2, red or dark blue shaded isotherms indicate "high stess", while light blue or yellow isotherms represent "low stress" areas. Thus, the relatively large area of dark blue shading in FIG. 1 indicates a "high stress" individual, while the large areas of light blue and yellow shaded areas in FIG. 2 represents a "low stress" individual.

The probabilities of conceiving a male or female child have been determined empirically from the above information, as follows:

In the case of stress values in the "high" range for both the father and mother, the probability of conceiving a male child is approximately 80%, and the probability of conceiving a female child is approximately 20%.

In the case of high stress values for one of the mother or the father, and low stress values for the other of the mother or the father, the probability of having a male child is also 80%, and the probability of having a female child is 20%.

In the case of low stress values for both the mother and father, the probability of having a male child is 20%, and the probability of having a female child is 80%. When very low stress readings are obtained from the scan, the probabilities of having a male or female child remain the same, but the possibility of infertility or miscarriage is increased. Very low stress readings are indicated by a black scan, or one with very little blue.

Of course, stress levels can change, and are subject to alteration for various reasons. Thus, these values may represent long-term traits of an individual or episodic occurrences as a result of externally-imposed conditions. These percentages are approximate. It is believed that the range of variation with the "high" and "low" stress levels is between 70% and 90%. These probabilities compare favorably with the percentage success rates achieved by the sperm separation technique described above.

Even if the probabilities are no better than those of the sperm separation technique, the vastly reduced cost and ease of use of the method provide substantial advantages.

With this information, a couple can make an informed decision about whether to attempt conception. If the probabilities favor the conception of a child having the desired sex, then conception is attempted. If the probabilities do not favor the conception of a child having the desired sex, then the parents may decide not to have further children, or may decide to attempt an alteration of the stress levels indicated by the thermograph.

While further research must be done in this area, various types of stress-modifying medications can be prescribed by a physician, or mood-altering exercises such as meditation or alpha-feedback practice an be attempted. Additional thermographs can easily be taken with little additional expense to determine the effectiveness of these efforts. In any case, these efforts are substantially less invasive and expensive than typical semen extraction techniques.

A method of increasing the probability of a female parent conceiving a child of the desired sex by use of infrared radiation analysis is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A method of predicting whether a woman will conceive either a male child or a female child, comprising the steps of:

(a) determining an infrared body temperature of the father using data obtained by a medical thermograph;

(b) determining an infrared body temperature of the mother using data obtained by the medical thermograph;

(c) categorizing the determined infrared body temperatures of the mother and the father as either "high" or "low" according to a predetermined categorization criteria;

(d) correlating the infared body temperatures of the mother and the father according to the categorization criteria wherein:

(i) in the case of high temperature for both the mother and the father, the probability of a male child is greater than the probability of a female child;

(ii) in the case of high temperature for one of the mother or the father and low temperature for the other of the mother or the father, the probability of a male child is greater than the probability of a female child; and (iii) in the case of low temperature for both the mother and the father, the probability of a male child is less than the probability of a female child.

* * * * *